United States Patent
Kamal et al.

(10) Patent No.: US 9,280,366 B2
(45) Date of Patent: Mar. 8, 2016

(54) ADAPTIVE APPLICATION OF ACCESSORY DEVICE SETTINGS

(71) Applicant: Cellco Partnership, Basking Ridge, NJ (US)

(72) Inventors: Ashfaq Kamal, Norristown, PA (US); Brigitte Bastaldo-Tsampalis, Bridgewater, NJ (US); Rita Sadhvani, Watchung, NJ (US); Manuel E Caceres, Basking Ridge, NJ (US); Ioannis Tsampalis, Bridgewater, NJ (US)

(73) Assignee: Cellco Partnership, Basking Ridge, NJ (US)

( * ) Notice: Subject to any disclaimer, the term of this patent is extended or adjusted under 35 U.S.C. 154(b) by 26 days.

(21) Appl. No.: 14/058,942

(22) Filed: Oct. 21, 2013

(65) Prior Publication Data

US 2015/0113262 A1   Apr. 23, 2015

(51) Int. Cl.
*G06F 3/00* (2006.01)
*G06F 9/445* (2006.01)
*A61B 5/00* (2006.01)
*A61B 5/11* (2006.01)

(52) U.S. Cl.
CPC .......... *G06F 9/44505* (2013.01); *A61B 5/7275* (2013.01); *A61B 5/002* (2013.01); *A61B 5/1113* (2013.01)

(58) Field of Classification Search
CPC ... H04L 12/24; H04L 12/281; H04L 12/2803; A61B 5/021; A61B 5/1123; A61B 5/7275; A61B 5/1113; A61B 5/002; G06F 9/44505
USPC .................................................. 710/8, 14
See application file for complete search history.

(56) References Cited

U.S. PATENT DOCUMENTS

| | | | |
|---|---|---|---|
| 2006/0064533 A1* | 3/2006 | Rael et al. | 710/310 |
| 2009/0316671 A1* | 12/2009 | Rolf et al. | 370/338 |
| 2013/0172691 A1* | 7/2013 | Tran | 600/301 |
| 2014/0297738 A1* | 10/2014 | King | 709/204 |
| 2015/0120000 A1* | 4/2015 | Coffey et al. | 700/13 |

OTHER PUBLICATIONS

Verizon Wireless, "Belkin @ TV Plus", http://www.verizonwireless.com/beta/accessories/belkin-tv-plus/#reviews, 4 pages, Sep. 27, 2013 (print date).

(Continued)

*Primary Examiner* — Ernest Unelus

(57) ABSTRACT

A system for adaptive application of device settings is disclosed. In the system, a first device may receive information identifying settings that are applied to one or more second devices. The settings may correspond to interactions, by a user, with the one or more second devices over a period of time. The one or more second devices be may non-mobile devices associated with one or more facilities. The first device may determine information identifying one or more conditions, associated with environmental conditions or conditions associated with the user's mood or physical state, under which the settings are applied to the one or more second devices; store information that correlates the settings of the one or more second devices with the one or more conditions; determine that at least one of the one or more conditions is met; and apply the settings to the one or more second devices.

20 Claims, 11 Drawing Sheets

(56) References Cited

OTHER PUBLICATIONS

Verizon Wireless, "Belkin WeMo Lightswitch", http://www.verizonwireless.com/beta/accessories/belkin-wemo-lightswitch/#reviews, Jul. 22, 2013, 3 pages.

Verizon Wireless, "Belkin NetCam HD Wi-Fi- Camera", http://www.verizonwireless.com/beta/accessories/belkin-netcam-hd-wifi-camera/#reviews, Sep. 23, 2013, 3 pages.

Verizon Wireless, "Nest Thermostat", Oct. 2, 2013, 2 pages.

Fitbit Inc., "Outsmart your weight with Aria™", Jan. 26, 2013, 6 pages.

Hanlon, "LG Internet Refrigerator", Jul. 1, 2002, 3 pages.

Samsung, "Samsung Introduces GALAXY Gear, a Wearable Device to Enhance the Freedom of Mobile Communications", Sep. 5, 2013, 2 pages.

Verizon Wireless, "Up by Jawbone®—(Medium)—Black", http://www.verizonwireless.com/beta/accessories/up-by-jawbone-medium-black/#reviews, Sep. 23, 2013, 3 pages.

Verizon Wireless, "Vehicle Diagnostics by Delphi—Give your Vehicle a Voice", 4 pages, Sep. 27, 2013 (print date).

Bla1ze, "Viper Announces SmartStart 3.0: the Cloud-Connected Car", Jan. 10, 2012, 7 pages.

Wikipedia, "Home Automation", http://en.wikipedia.org/wiki/Home_automation, Sep. 9, 2013, 10 pages.

\* cited by examiner

| Program ID 410 | Conditions 420 | Device Settings 430 |
|---|---|---|
| 1 | -Day of week (50)<br>-Time (50)<br>-Mood (100) | Device 1 Settings<br>Device 2 Settings |
| 2 | -Outside Temp (50)<br>-Time (50) | Device 3 Settings<br>Device 4 Settings |
| 3 | -Location (50)<br>-Time (50)<br>-Mood (100) | Device 5 Settings<br>Device 6 Settings<br>Device 7 Settings |

ADAPTIVE APPLICATION OF ACCESSORY DEVICE SETTINGS

BACKGROUND

Accessory devices, such as network-enabled consumer electronics, appliances, etc. can be controlled by user devices within a network to power on/off the accessory devices and to select device settings that cause the accessory devices to perform various functions. Manually applying device settings to multiple accessory devices can be time-consuming, particularly when the settings are to be individually applied to each accessory device in accordance with a user's habits and schedule.

BRIEF DESCRIPTION OF THE DRAWINGS

FIG. 4 illustrates an example data structure that may be stored by one or more devices in the environment of FIG. 2;

DETAILED DESCRIPTION OF THE PREFERRED EMBODIMENTS

Figure 1A:
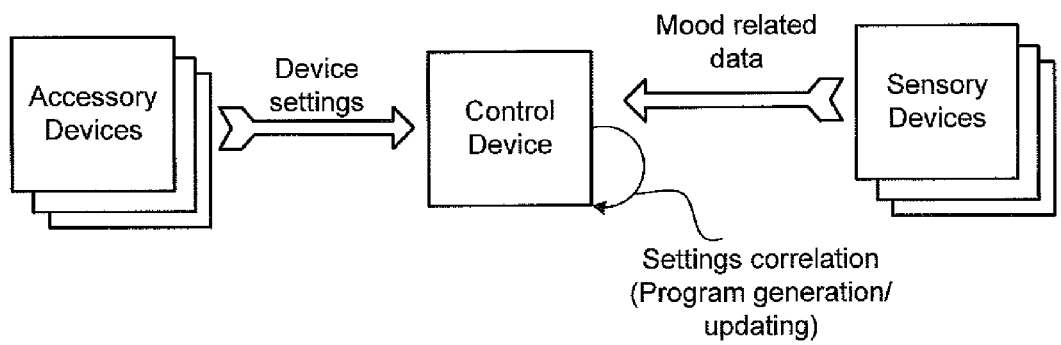
FIGS. 1A-1B illustrate an example overview of an implementation described herein.

The following detailed description refers to the accompanying drawings. The same reference numbers in different drawings may identify the same or similar elements.

Systems and/or methods, as described herein, may identify device settings (e.g., power on/off settings, functional settings, etc.) of one or more accessory devices and may correlate the settings with particular surrounding/environmental conditions associated with an environment in which the one or more accessory devices are implemented. In some implementations, the device settings may relate to the activity of the one or more accessory devices (e.g., a user's interaction with the one or more accessory devices). In some implementations, a control device may apply the settings to the one or more accessory devices when the particular environmental conditions (hereinafter referred to as "conditions") are met. For example, a control device may identify settings of an accessory device, such as a light controller, a power controller, a home appliance, a consumer electronics device, or the like, and may identify conditions under which the settings are applied.

In some implementations, the conditions may relate to a user's schedule, a time of day, weather information, or the like. In some implementations, the conditions may also relate to biometrics information for a user that corresponds to the user's mood and/or physical state. In some implementations, the control device may apply particular settings to an accessory device based on the conditions (e.g., based on a time of day, the user's mood, etc.). For example, for an accessory device that includes a light controller, the control device may apply a setting that controls a brightness level of a light connected to the light controller based on a time of day, the user's mood, and/or some other condition.

For an accessory device that includes a home appliance, such as a beverage machine, the control device may apply a setting that directs the beverage machine to create a particular beverage based on a user's schedule, the user's mood, and/or some other condition. For an accessory device that includes a consumer electronics device, such as a television, the control device may apply a setting that directs the television to display a particular channel based on the user's schedule and/or some other condition.

In some implementations, the control device may adapt to the user's habits by identifying changes to the devices settings of an accessory device (e.g., when a user manually changes the settings), and may modify a correlation between the device settings and the conditions under which the device settings are applied. As a result, settings of accessory devices may be automatically applied (e.g., based on the user's past habits/behaviors) to power on/off the accessory devices and/or cause the accessory devices to perform particular functions in a particular order based on a user's schedule, a user's mood, a time of day, weather information, geographic location, and/or some other condition.

Figure 1B:
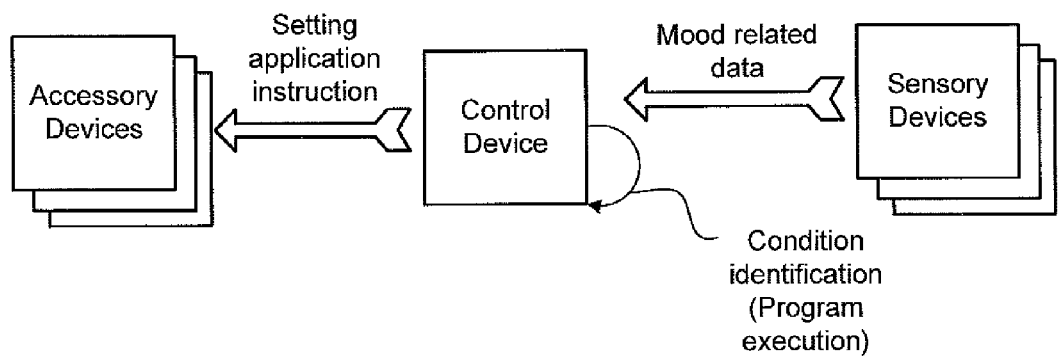

FIGS. 1A-1B illustrate an example overview of an implementation described herein. As shown in FIG. 1A, a control device may receive device settings from one or more accessory devices. In some implementations, the control device may monitor the settings that relate to the usage and/or activity of the one or more accessory devices. For example, for an accessory device that includes a light controller, the control device may monitor a setting of the light controller that relates to a brightness level of a light connected to the light controller. For a home appliance, such as a beverage maker, the control device may monitor a setting of the beverage maker that identifies a particular beverage that is being prepared. For an accessory device that includes a consumer electronics device, such as a television, the control device may monitor settings that identify a particular channel that the television displays.

In some implementations, the control device may correlate the settings of the one or more accessory devices to particular conditions under which the one or more accessory devices are set to the settings. For example, the controller device may correlate the settings to information identifying a particular day of the week, a particular time of day, weather information, or the like. Additionally, or alternatively, the controller device may correlate the settings to mood-related data received from one or more sensory devices (e.g., biometrics data and/or some other information that relates to a user's mood).

Based on correlating the settings with the conditions, the control device may generate a program that may execute when the conditions are later met. For example, referring to FIG. 1B, the control device may identify that the conditions have been met, and may execute the program to apply the device settings to the accessory devices. In some implementations (e.g., when a program exists for a particular set of conditions), the control device may update the program with updates to the device settings.

As an example, assume that, the control device receives device settings for a light controller accessory device (e.g., a brightness level setting of 100% brightness), a beverage maker accessory device (e.g., a setting to prepare a particular beverage), and a television accessory device (e.g., a setting of a particular channel). Further, assume that the control device receives these settings under certain conditions, or correlates these settings with certain conditions, such as a particular time of day (e.g., 7 AM), and when one or more sensory devices provide mood-related data that indicate that a user of the accessory devices is in a "Tired" mood. Given these assumptions, the control device may generate a program that correlates the device settings with the particular conditions (or update a program that exists for the conditions). At a later time, the control device may identify that the particular conditions have been met, such as when the control device receives mood-related data that indicates that the user is in a "Tired" mood and when the time is 7 AM. Based on identifying that the particular conditions have been met, the control device may execute the program to apply the settings to the accessory devices.

In some implementations, the control device may generate a program, as described above. Additionally, or alternatively, a user may provide a program to the control device (e.g., a program that directs the control device to apply device settings to particular accessory devices based on particular conditions, such as conditions relating to the user's schedule and/or mood). In some implementations, the control device may update a program (either a generated program or a user provided program) to adapt to a user's habits by monitoring the device settings of accessory devices and the conditions under which the device settings are applied. In some implementations, a program may identify a sequence in which to apply the device settings. As a result, settings of accessory devices may be automatically applied to power on/off the accessory devices and/or cause the accessory devices to perform particular functions in a particular order based on a user's schedule, a user's mood, a time of day, weather information, geographic location, and/or some other condition.

Figure 2:
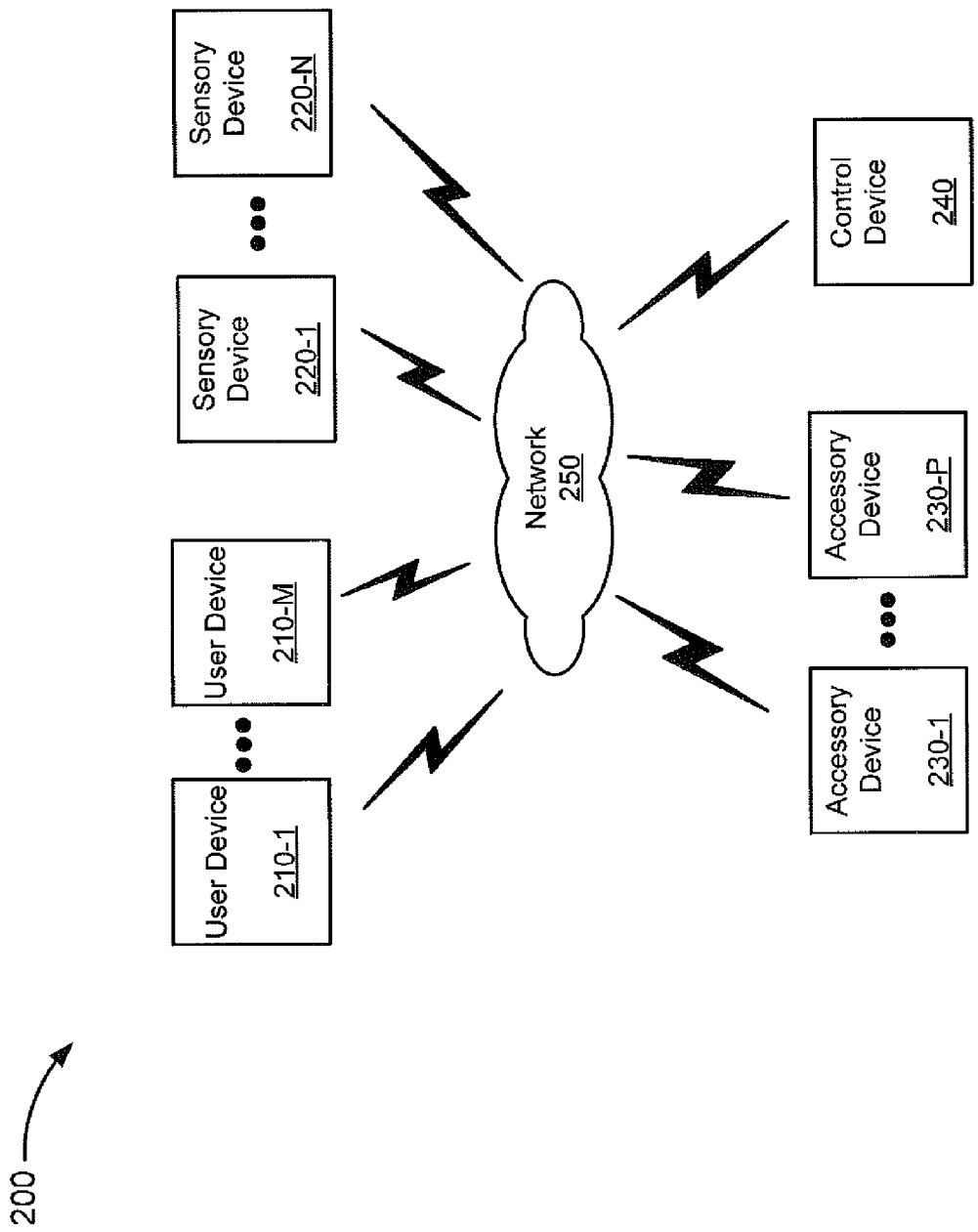
FIG. 2 illustrates an example environment in which systems and/or methods, described herein, may be implemented.

FIG. 2 is a diagram of an example environment 200 in which systems and/or methods described herein may be implemented. As shown in FIG. 2, environment 200 may include user devices 210-1, . . . , 210-M (where M≥1), sensory devices 220-1, . . . , 220-N (where N≥1), accessory devices 230-1, . . . , 230-P (where P≥1), control device 240, and network 250.

User device 210 may include a device capable of communicating via a network, such as network 250. For example, user device 210 may correspond to a mobile communication device (e.g., a smart phone or a personal digital assistant (PDA)), a portable computer device (e.g., a laptop or a tablet computer), a desktop computing device, a gaming device, a set-top box, and/or another type of device.

In some implementations, user device 210 may provide a user generated program to control device 240 (e.g., a program that directs control device 240 to apply particular settings to accessory device 230 when particular conditions are met). For example, user device 210 may include an application that may be used to generate a program and provide the program to control device 240. In some implementations, user device 210 may access control device 240 to generate a program via an application programming interface (API) on control device 240. In some implementations, user device 210 may provide an instruction to control device 240 to execute a particular program. Additional details regarding programs that a user may generate via user device 210 are described in greater detail below with respect to FIG. 4. In some implementations, user device 210 may function as sensory device 220 to receive mood-related information (e.g., biometrics information, etc.).

Sensory device 220 may include a biometrics monitoring device, a movement-tracker, a sleep-tracker, or some other type of device that may gather data associated with a user's mood. For example, sensory device 220 may include a heart-rate monitor, a camera device, a wrist-band, a watch, or the like. In some implementations, sensory device 220 may gather mood-related data (e.g., a user's physiological measurements), such as heart-rate information, blood-pressure information, user temperature, movement information, calorie burning information, speech pattern information, tone of voice, voice stress analysis data, and/or some other data that identifies the mood and/or physical state of the user.

In some implementations, sensory device 220 may analyze the mood-related data to identify the user's mood and/or physical state and provide information identifying the user's mood and/or physical state to user device 210 and/or control device 240. For example, sensory device 220 may store mood profiles that identify a user's mood based on the mood-related data. As an example, sensory device 220 may store a mood profile with a description of "Tired" when information identifying a heart-rate, blood-pressure, user temperature, etc., are within particular ranges. In some implementations, the particular ranges, associated with a mood profile, may be user defined or predefined.

In some implementations, sensory device 220 may gather conditions information relating to weather, time/date, geographic location, lighting intensity, room temperature, noise/sound level, or the like and may provide the conditions information to control device 240.

Accessory device 230 may include a device capable of communicating with a network, such as network 250. For example, accessory device 230 may include a light controller, a power controller, a thermostat, a home appliance (e.g., a beverage machine, a refrigerator, a vacuum cleaner, etc.), a consumer electronics device (e.g., a television, a music player, a scent diffuser, etc.), or the like. In some implementations, a user of accessory device 230 may apply a setting to accessory device 230 (e.g., remotely via user device 210 and/or manually via physical and/or virtual buttons associated with accessory device 230). Additionally, or alternatively, control device 240 may apply a setting to accessory device 230 based on executing a program. In some implementations, a setting may correspond to powering on/off accessory device 230, and/or directing accessory device 230 to perform a task. In some implementations, accessory device 230 may be a non-mobile device associated with a particular facility or a particular group of facilities.

Control device 240 may include a computing device, such as a server device, or a collection of server devices. In some implementations, control device 240 may apply device settings to accessory device 230 to power on/off accessory device 230 and/or to cause accessory device 230 to perform a task. In some implementations, control device 240 may apply the device settings based on a program that identifies conditions under which to apply the device settings. For example, the program may identify that a particular accessory device 230 is to be powered on in accordance with a user's schedule, and/or when the user is in a particular mood (e.g., based on mood-related data received from user device 210 and/or sensory device 220). As described in greater detail below with respect to FIG. 5, control device 240 may identify a particular program to use to apply the device settings when conditions for multiple programs have been met. In some implementations, control device 240 may monitor device settings of accessory device 230 and may generate a program that correlates the device settings of accessory device 230 with particular conditions. Additionally, or alternatively, control device 240 may update an existing program that identifies device settings for a given set of conditions (e.g., when device settings are modified by a user of accessory device 230). In some implementations, one or more accessory devices 230 may connect to a single control device 240 in a particular facility, such as a home, an office, or the like.

Network 250 may include one or more wired and/or wireless networks. For example, network 250 may include a cellular network (e.g., a second generation (2G) network, a third generation (3G) network, a fourth generation (4G) network, a fifth generation (5G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, network 250 may include a local area network (LAN), a Zigbee network, a Bluetooth network, a near-field communications (NFC) network, a wide area network (WAN), a metropolitan network (MAN), a telephone network (e.g., the Public Switched Telephone Network (PSTN)), an ad hoc network, a managed IP network, a virtual private network (VPN), an intranet, the Internet, a fiber optic-based network, and/or a combination of these or other types of networks.

In some implementations, network 250 may include a first network, such as a sensory network, via which sensory devices 220 and control device 240 may communicate. For example, sensory devices 220 may provide physiological measurements to control device 240 via the sensory network. In some implementations, network 250 may include a second network via which accessory devices 230 and control device 240 may communicate (e.g., such that control device 240 may apply settings to accessory devices 230 based on particular conditions). In some implementations, control device 240 may communicate with sensory devices 220 using a first command language and may communicate with accessory devices 230 using a second command language. Additionally, or alternatively, control device 240 may communicate with sensory devices 220 and accessory devices 230 using a common command language. In some implementations, control device 240 may implement a shell command language and/or a command language interpreter when communicating with sensory devices 220 and accessory devices 230.

The quantity of devices and/or networks, illustrated in FIG. 2, is not limited to what is shown. In practice, there may be additional devices and/or networks; fewer devices and/or networks; different devices and/or networks; or differently arranged devices and/or networks than illustrated in FIG. 2. Also, in some implementations, one or more of the devices of environment 200 may perform one or more functions described as being performed by another one or more of the devices of environment 200. Devices of environment 200 may interconnect via wired connections, wireless connections, or a combination of wired and wireless connections.

Figure 3:
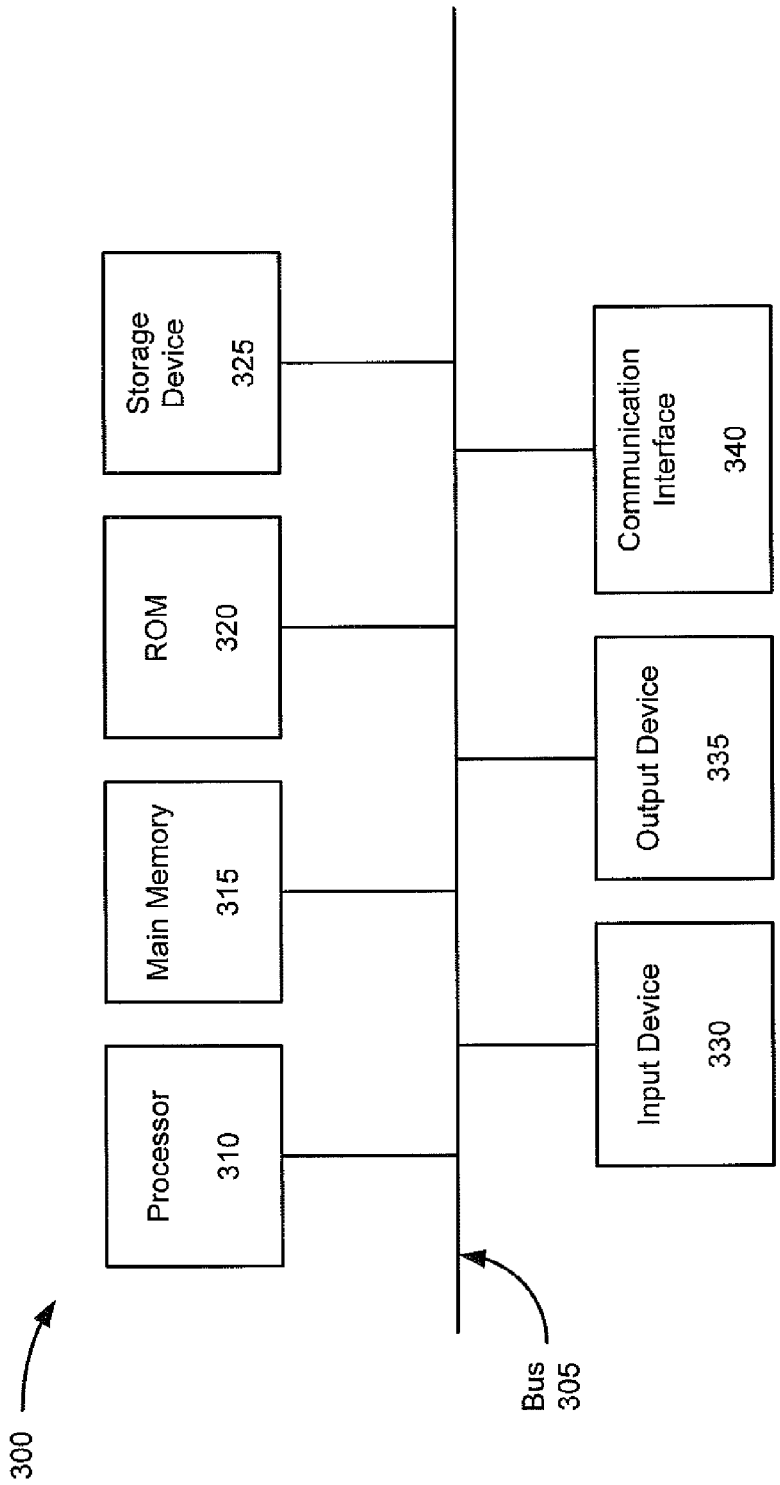
FIG. 3 illustrates example components of a device that may be used within the environment of FIG. 2.

FIG. 3 illustrates example components of a device 300 that may be used within environment 200 of FIG. 2. Device 300 may correspond to user device 210, sensory device 220, accessory device 230, and/or control device 240. Each of user device 210, sensory device 220, accessory device 230, and/or control device 240 may include one or more devices 300 and/or one or more components of device 300.

As shown in FIG. 3, device 300 may include a bus 305, a processor 310, a main memory 315, a read only memory (ROM) 320, a storage device 325, an input device 330, an output device 335, and a communication interface 340.

Bus 305 may include a path that permits communication among the components of device 300. Processor 310 may include a processor, a microprocessor, an application specific integrated circuit (ASIC), a field programmable gate array (FPGA), or another type of processor that interprets and executes instructions. Main memory 315 may include a random access memory (RAM) or another type of dynamic storage device that stores information or instructions for execution by processor 310. ROM 320 may include a ROM device or another type of static storage device that stores static information or instructions for use by processor 310. Storage device 325 may include a magnetic storage medium, such as a hard disk drive, or a removable memory, such as a flash memory.

Input device 330 may include a component that permits an operator to input information to device 300, such as a control button, a keyboard, a keypad, or another type of input device. Output device 335 may include a component that outputs information to the operator, such as a light emitting diode (LED), a display, or another type of output device. Communication interface 340 may include any transceiver-like component that enables device 300 to communicate with other devices or networks. In some implementations, communication interface 340 may include a wireless interface, a wired interface, or a combination of a wireless interface and a wired interface.

Device 300 may perform certain operations, as described in detail below. Device 300 may perform these operations in response to processor 310 executing software instructions contained in a computer-readable medium, such as main memory 315. A computer-readable medium may be defined as a non-transitory memory device. A memory device may include memory space within a single physical storage device or memory space spread across multiple physical storage devices.

The software instructions may be read into main memory 315 from another computer-readable medium, such as storage device 325, or from another device via communication interface 340. The software instructions contained in main memory 315 may direct processor 310 to perform processes that will be described later. Alternatively, hardwired circuitry may be used in place of or in combination with software instructions to implement processes described herein. Thus, implementations described herein are not limited to any specific combination of hardware circuitry and software.

In some implementations, device 300 may include additional components, fewer components, different components, or differently arranged components than are shown in FIG. 3.

FIG. 4 illustrates an example data structure 400 that may be stored by one or more devices in environment 200, such as control device 240. In some implementations, data structure 400 may be stored in a memory of control device 240. In some implementations, data structure 400 may be stored in a memory separate from, but accessible by, control device 240. In some implementations, data structure 400 may be stored by some other device in environment 200, such as user device 210, sensory device 220, and/or accessory device 230. A particular instance of data structure 400 may contain different information and/or fields than another instance of data structure 400. In some implementations, each row in data structure 400 may include information identifying a program that may be generated, received, updated, and/or executed by control device 240.

As shown in FIG. 4, data structure 400 may include program identifier (ID) field 410, conditions field 420, and/or device settings field 430.

Program ID field 410 may store an identifier of a particular program stored by data structure 400. For example, program ID field 410 may store a string of characters, of any format and length, to uniquely identify the particular program. In some implementations, control device 240 may assign a program ID when receiving a program from user device 210 and/or when generating a program.

Conditions field 420 may store information identifying conditions under which device settings of accessory devices 230 are applied. For example, conditions field 420 may store conditions corresponding to a user's schedule (e.g., a day of the week, a day in the year, a time of day, etc.). Additionally, or alternatively, conditions field 420 may store conditions relating to a user's mood, physical state, weather information, geographic location information, etc. Additionally, or alternatively, conditions field 420 may store conditions relating to the presence of a particular user device 210 (e.g., based on a device identifier of user device 210, a network address of user device 210, or the like).

In some implementations, particular conditions may include condition scores, such that a corresponding program may execute when only some of the conditions are met. For example, a particular program may execute when a condition score satisfies a threshold. In conditions field 420, the weightings are shown in parenthesis and may add to a condition score when the condition is met. For example, for program ID 1, a condition identifying a day of the week may include a condition score of 50, a condition identifying a time may include a condition score of 50, and a condition identifying a user's mood may include a condition score of 100. Assuming that a condition score of 100 satisfies a threshold at which program ID 1 may be executed, control device 240 may execute the program when the condition identifying the day of the week is met and when the condition identifying the time is met (e.g., since a condition score of 100 would apply). Alternatively, control device 240 may execute the program when the condition identifying the user's mood is met, even if the other two conditions are not met (e.g., since a condition score of 100 would apply when only the condition identifying the user's mood is met).

Device settings field 430 may store information identifying device settings of one or more accessory devices 230 that are to be applied when a corresponding program is executed. In some implementations, device settings field 430 may store information identifying updated device settings (e.g., device settings manually updated by a user) corresponding to a set of conditions (e.g., such that when the corresponding program is executed, the updated device settings are applied to accessory devices 230). In some implementations, device settings field 430 may store device settings to direct control device 240 to power on/off accessory device 230 and/or cause accessory device 230 to perform a particular task. In some implementations, device settings field 430 may store device settings in a particular sequence corresponding to a sequence in which control device 240 is to apply the device settings to accessory devices 230 (e.g., to power on and/or power off accessory devices 230 in a particular sequence).

In some implementations, data structure 400 may store a program for each set of conditions. As a result, different programs may execute as conditions change, thereby causing different settings to be applied to accessory devices 230 as conditions change. Further, when device settings are updated (e.g., manually updated by a user of accessory devices 230 corresponding to the user's habits/behaviors), those updates may be stored by device settings field 430 in association with a corresponding set of conditions. That is, data structure 400 may store and update device settings that correspond to changes in the user's habits/behaviors.

While particular fields are shown in a particular format in data structure 400, in practice, data structure 400 may include additional fields, fewer fields, different fields, or differently arranged fields than are shown in FIG. 4. Also, FIG. 4 illustrates examples of information stored by data structure 400. In practice, other examples of information stored by data structure 400 are possible.

Figure 5A:
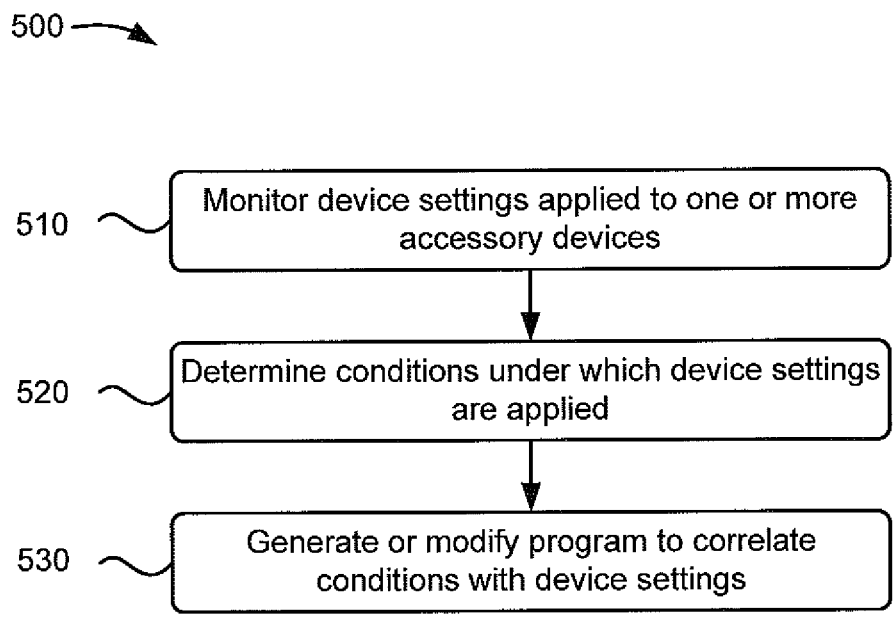
FIGS. 5A-5B illustrate flowcharts of an example process for correlating conditions with device settings and executing a device program.
Figure 5B:
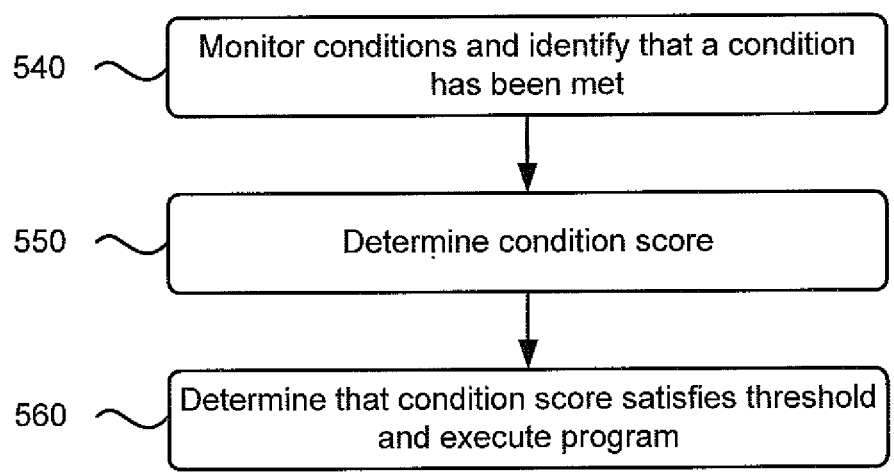

FIGS. 5A-5B illustrate flowcharts of an example process 500 for correlating conditions with device settings and executing a device program. In one implementation, process 500 may be performed by one or more components of control device 240. In another implementation, some or all of blocks of process 500 may be performed by one or more components of another device in environment 200 (e.g., user device 210, sensory device 220, and/or accessory device 230), or a group of devices including or excluding control device 240.

As shown in FIG. 5A, process 500 may include monitoring device settings applied to one or more accessory devices (block 510). For example, control device 240 may monitor device settings of accessory device 230 by receiving the device settings at regular intervals (e.g., every minute, every five minutes, every hour, etc.). In some implementations, control device 240 may receive the device settings when the device settings on accessory device 230 are updated.

In some implementations, the device settings may be applied to accessory device 230 in accordance with a program executed by control device 240 (e.g., a program received by control device 240 from a user or a program generated by control device 240). Additionally, or alternatively, device settings applied to accessory device 230 may be manually applied by the user of accessory device 230. In some implementations, control device 240 may monitor the activity of accessory devices 230 and may monitor a sequence in which settings are applied to accessory devices 230 (e.g., a sequence in which accessory devices 230 are powered on/off, instructed to perform particular tasks, etc.). For example, control device 240 may monitor the activity of accessory devices 230 (e.g., based on instructions received from a user of accessory devices 230), and, as described in greater detail below, may generate a program that stores the device settings, corresponding to the activity of accessory devices 230, such that device settings may be automatically applied to accessory devices 230 in the future when particular conditions are met. In some implementations, control device 240 may monitor the activity of accessory device 230 by receiving an indication, from accessory device 230, when a setting is applied or changed to accessory device 230.

Process 500 may also include determining conditions under which the device settings are applied (block 520). For example, control device 240 may determine one or more conditions under which the device settings are applied to accessory device 230. In some implementations, control device 240 may identify a time of day, a day of the week, weather information, geographic location information, mood-related information (e.g., based on information received from sensory device 220), and/or some other condition under which the device settings are applied to accessory device 230.

Process 500 may further include generating or modifying a program to correlate the conditions with device settings (block 530). For example, control device 240 may store a program ID (e.g., in program ID field 410) and a set of conditions (e.g., in conditions field 420) corresponding to program ID and the conditions identified in process block 520. Further, control device 240 may store the device settings in device settings field 430 corresponding to the set of conditions. In some implementations, control device 240 may identify that a program ID exists for a particular set of conditions (e.g., corresponding to a program previously generated by control device 240 or a program generated by a user via user device 210 and/or via a user interface of control device 240). In some implementations (e.g., when a program ID exists for a particular set of conditions), control device 240 may update the device settings for that program such that updating device settings may be applied when the particular set of conditions is met (e.g., when a condition score satisfies a particular threshold).

In some implementations, control device 240 may determine the conditions during which the device settings are applied to accessory device 230. For example, control device 240 may determine the conditions have changed even if the device settings remain unchanged. In some implementations, control device 240 may generate or update a program for a set of conditions that reflect the device settings under the set of conditions even when the device settings remain unchanged from one set of conditions to another.

In some implementations, control device 240 may track a number of times that the device settings have been applied under a particular set of conditions. In some implementations, control device 240 may generate or update a program, associated with a particular set of conditions, when the number of times that the device settings have been applied under a particular set of conditions satisfies a particular threshold. For example, control device 240 may generate or update a program based on identifying a pattern of conditions under which device settings are applied. In some implementations, the pattern may be identified when the number of times that the device settings have been applied under a particular set of conditions satisfies the particular threshold.

In some implementations, the particular threshold may be selected by a user and may correspond to a sensitivity setting selected by the user. For example, for a relatively high sensitivity setting, the particular threshold may be lower than for a relatively lower sensitivity setting. That is, a relatively higher sensitivity may cause control device 240 to more quickly identify a pattern of conditions under which device settings are applied than a relatively lower sensitivity. The relatively lower sensitivity may prevent control device 240 from erroneously identifying a pattern, for example, when a device setting is applied as an isolated incident rather than as part of a pattern.

In some implementations, control device 240 may provide an alert to user device 210 including a suggestion to generate or update a program. In some implementations, control device 240 may generate or update the program based on receiving an instruction from user device 210 in response to receiving the suggestion to generate or update the program.

Referring to FIG. 5B, process 500 may also include monitoring conditions and identifying that a condition has been met (block 540). For example, control device 240 may monitor particular conditions, such as conditions relating to a time of day, a day of the week, etc., via a clock, calendar, and/or timekeeping device associated with control device 240. In some implementations, control device 240 may periodically receive information associated with conditions from sensory device 220 (e.g., information relating to a user's mood, information relating to the weather, information relating to a room temperature or the like). In some implementations, control device 240 may identify that a condition has been met when a condition that has been identified by control device 240 matches a condition stored by conditions field 420 in data structure 400.

Process 500 may further include determining a condition score (block 550). For example, control device 240 may determine a condition score based on identifying that a condition has been met and based on condition score information stored by conditions field 420. As an example, assume that control device 240 determines that a condition relating to a user's mood has been met and that the condition relating to the user's mood includes a condition score of 100. Further, assume, that control device 240 determines that a condition relating to a day of the week has been met and that the condition relating to the day of the week includes a condition score of 50. Given these assumptions, control device 240 may determine a condition score of 150 (e.g., by summing the condition scores associated with the identified conditions).

In some implementations, control device 240 may assign condition scores to particular conditions. For example, control device 240 may assign a relatively greater condition score to a condition that is more related to the function of accessory device 230 than a condition that is less related to the function of accessory device 230. As an example, assume that accessory device 230 corresponds to a television. Given this assumption, control device 240 may assign a greater condition score to a condition relating to a time of day than to a condition relating to weather information (e.g., since information identifying a time of day may be more relevant than weather information for a device setting for a television, such as a channel number corresponding to a broadcast of a particular television program). As another example, assume that accessory device 230 corresponds to a thermostat device. Given this assumption, control device 240 may assign a greater condition score to a condition relating to weather information than to a condition relating to a time of day (e.g., since the weather information may be more relevant than time information for a device setting corresponding to a temperature at which the thermostat is set). In some implementations, a user may assign the condition scores when generating or modifying a program stored by control device 240.

Process 500 may also include determining that a condition score satisfies a threshold and executing a program (block 560). For example, control device 240 may determine that the condition score (e.g., as determined above in block 550) has satisfied a particular threshold. In some implementations, the particular threshold may be user selectable, and may include a default threshold that causes a program to execute when some or all conditions, associated with a program, are met. Based on determining that the condition score has been satisfied, control device 240 may execute a corresponding program, associated with the condition score, and apply device settings to accessory devices 230 (e.g., in a particular sequence as defined by the program) to power on/off accessory devices 230, and/or cause accessory devices 230 to perform a particular task.

As an example, assume that a particular program is associated with a condition identifying a day of the week (with a condition score of 50), a time (with a condition score of 50), and a user's mood (with the condition score of 100). Further, assume that the particular program may execute when the condition score satisfies a threshold of 100. Given these assumptions, the particular program may execute when the conditions identifying the day of the week and the time are met. Additionally, or alternatively, the particular program may execute when the condition identifying the user's mood is met.

In some implementations (e.g., when particular conditions for multiple programs have been met and the condition score has been satisfied for each set of conditions), control device 240 may execute a particular program whose condition score is greatest. In some implementations (e.g., when particular conditions for multiple programs have been met and the condition is equal for the multiple programs), control device 240 may execute a particular program based on priority information associated with each program. For example, assume program 1 is associated with a condition identifying a day of the week (with a condition score of 50), a time (with a condition score of 50), and a user's mood (with the condition score of 100). Further, assume that program 3 is associated with a condition identifying a geographic location (with a condition score of 50), a time (with a condition score of 50), and a user's mood (with the condition score of 100). Given these assumptions, a condition score of 100 may be determined for programs 1 and 3 when the condition identifying the user's mood is met, but when the other conditions of programs 1 and 3 are not met.

In some implementations, control device 240 may determine whether to execute program 1 or 3 based on a priority of program 1 and 3. In some implementations, the priority of the programs may be user selectable. Additionally, or alternatively, the priority of the programs may be proportional to a number of times that a program is executed. For example, control device 240 may log the number of times that a program is executed. In some implementations (e.g., when the number of times that multiple programs have been executed are equal and when condition scores of multiple programs are equal), control device 240 may select a particular program to execute based on a round-robin technique, a manual override based on user input, and/or some other technique.

Based on determining a particular program to execute, control device 240 may execute the particular program to apply device settings to accessory devices 230 in accordance with device settings identified in device settings field 430. For example, control device 240 may power on or power off accessory device 230. Additionally, or alternatively, control device 240 may apply a setting to direct accessory device 230 to perform a particular task. As an example, control device 240 may apply a setting to a television accessory device 230 to cause accessory device 230 to power on, and set to a particular television channel. As another example, control device 240 may apply a setting to a light controller accessory device 230 to direct accessory device 230 to output a particular voltage to a lighting device connected to accessory device 230 (e.g., to adjust the illumination output by the lighting device).

As described above, control device 240 may execute different programs as conditions change, thereby causing different settings to be applied to accessory device 230 as conditions change. As described above, a condition may correspond to the presence of a particular user device 210. For example, when a first user device 210 (e.g., user device 210-1) is present, but a second user device 210 (e.g., user device 210-2) is not present, control device 240 may execute a first program. When user device 210-1 and user device 210-2 are present, control device 240 may execute a second program (e.g., to apply settings to different accessory devices 230 in different sequences).

In some implementations, process 500 may repeat in order to monitor device settings that may be updated (e.g., manually by a user of accessory device 230), identify a set of conditions associated with the updated device settings, and modify a corresponding program associated with the set of conditions, such that when conditions are met (e.g., when a condition score satisfies a threshold), the program may execute to apply the updated device settings to accessory device 230.

While FIGS. 5A-5B show process 500 as including a particular quantity and arrangement of blocks, in some implementations, process 500 may include fewer blocks, additional blocks, or a different arrangement of blocks. Additionally, or alternatively, some of the blocks may be performed in parallel.

Figure 6A:
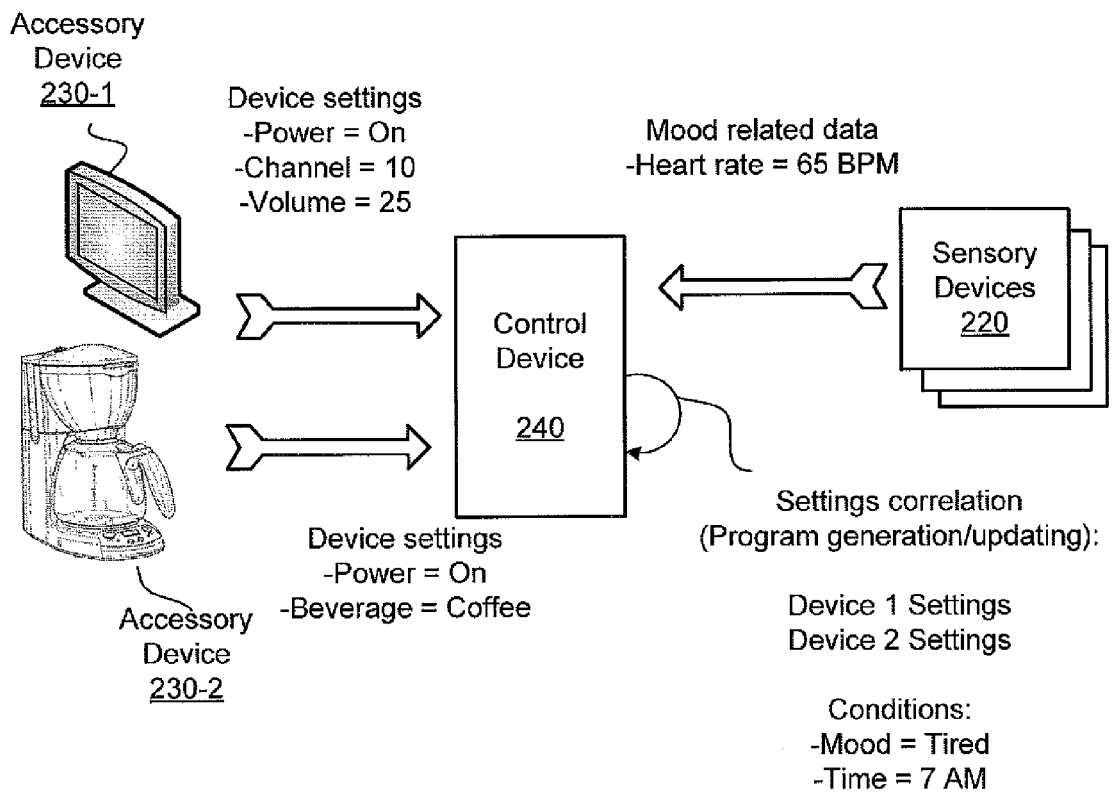
FIGS. 6A-6B illustrate an example implementation as described herein.
Figure 6B:
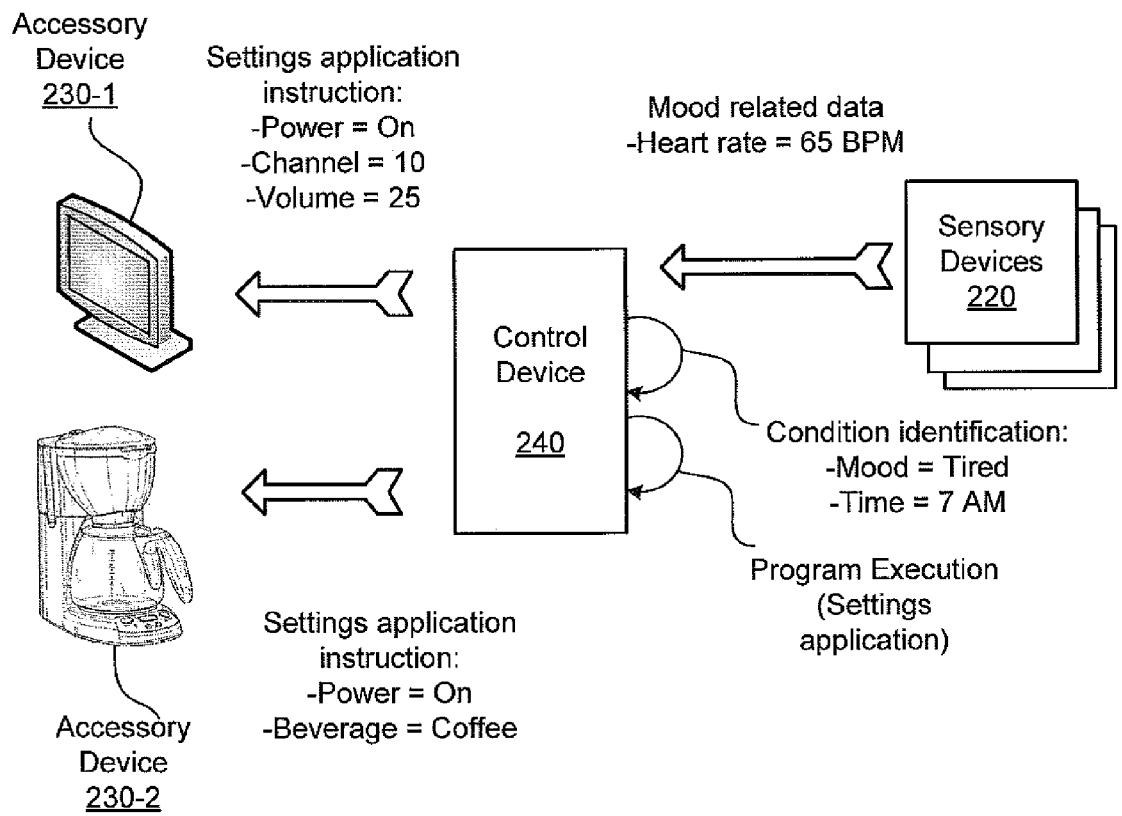

FIGS. 6A-6B illustrate an example implementation as described herein. In FIG. 6A, assume that accessory device 230-1 is a television, and that accessory device 230-2 is a beverage machine. As shown in FIG. 6A, control device 240 may receive device settings for accessory device 230-1 and accessory device 230-2. For example, for accessory device 230-1, control device 240 may receive device settings that indicate that accessory device 230-1 is powered on, set to channel 10, and set to a volume level of 25. For accessory device 230-2, control device 240 may receive device settings that indicate that accessory device 230-2 is powered on, and set to produce a coffee beverage. In some implementations, control device 240 may generate a program to correlate the device settings of accessory device 230-1 and accessory device 230-2 with conditions (e.g., a time of day, mood-related information received from sensory device 220, and/or some other condition). For example, control device 240 may correlate the device settings with a condition identifying mood-related information that corresponds to a "Tired" mood, and with a condition identifying a time of 7 AM.

At a later time, control device 240 may determine that the conditions have been met when receiving mood-related data corresponding to a particular mood (e.g., a "Tired" mood when sensory device 220 gathers physiological measurements corresponding to the "Tired" mood) at a particular time of day (e.g., 7 AM) and may execute the program to power on/off accessory devices 230 and to cause accessory devices 230 to perform tasks. For example, referring to FIG. 6B, control device 240 may receive mood-related data corresponding to a "Tired" mood at 7 AM, may identify that the conditions have been met, and execute the program to apply device settings to accessory device 230-1 and accessory device 230-2. As a result, device settings may be applied without user interaction and may be applied based on the user's habits.

In some implementations, control device 240 may provide an indication to user device 210 that control device 240 has identified that particular conditions have been met and that a particular program is to be executed. In some implementations, control device 240 may receive a cancellation and/or a snooze instruction from user device 210 to cancel or delay the execution of the program. In some implementations, the amount of time to delay the execution of the program may be selected by a user of user device 210. In some implementations, the amount of time to delay the execution of the program may correspond to a predetermined default amount of time.

While a particular example is shown in FIGS. 6A-6B, the above description is merely an example implementation. In practice, other examples are possible from what is described above in FIGS. 6A-6B.

Figure 7A:
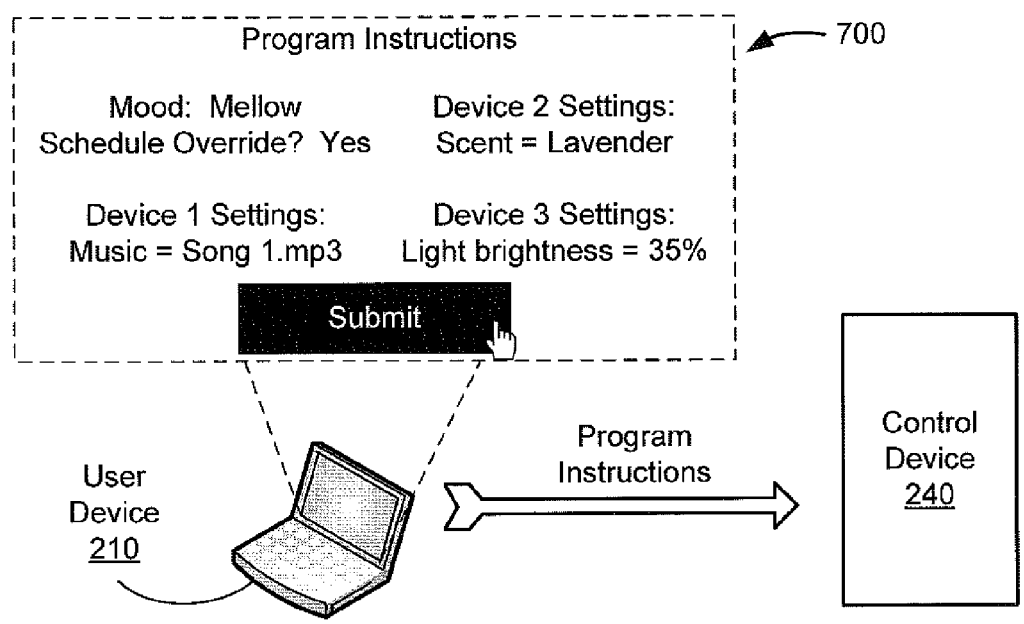
FIGS. 7A-7C illustrate an example implementation as described herein.
Figure 7B:
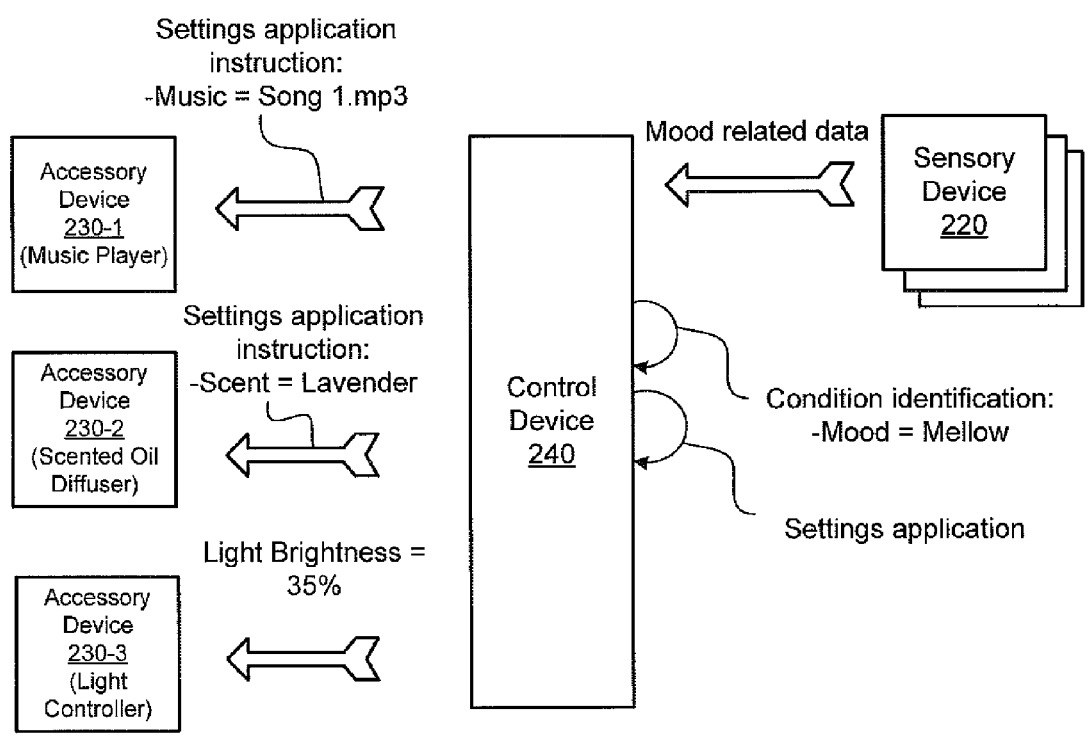
Figure 7C:
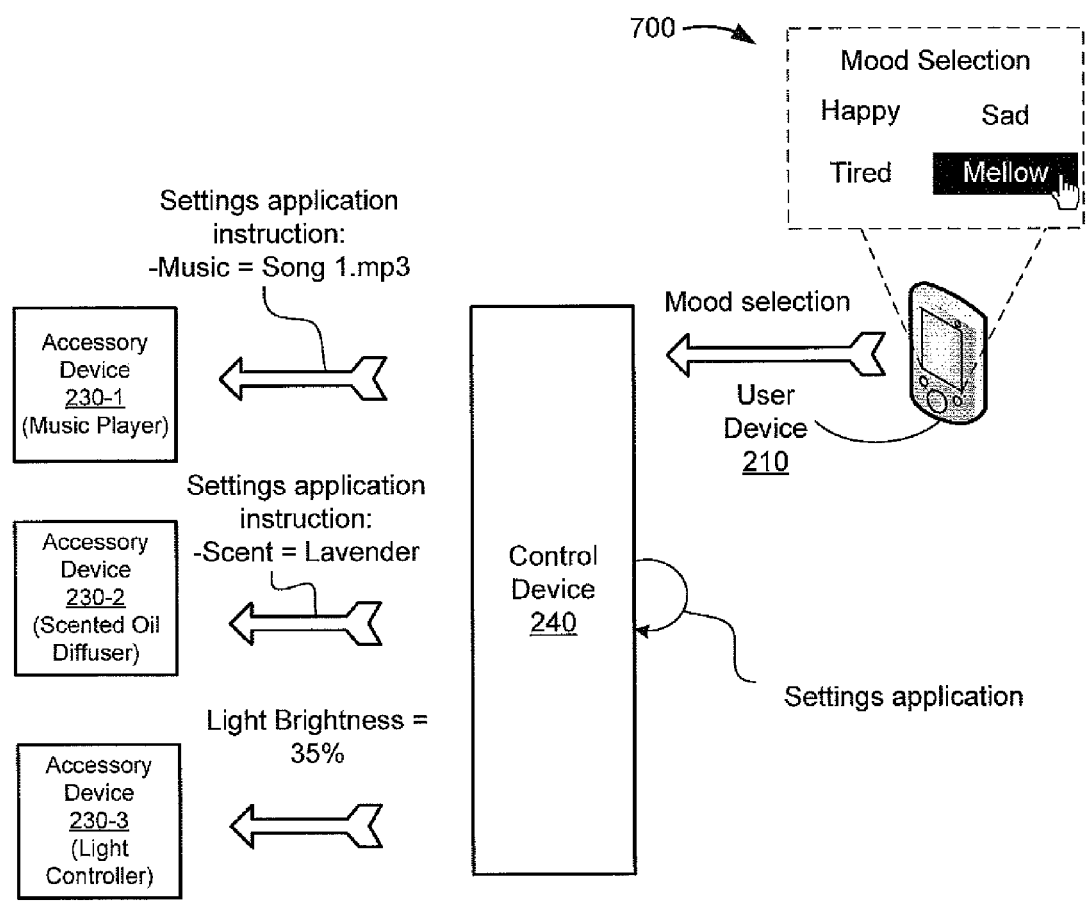

FIGS. 7A-7C illustrate an example implementation as described herein. As shown in FIG. 7A, a user may generate a program via interface 700 of user device 210 (e.g., a therapeutic program). For example, interface 700 may present options for the user to select program instructions that control device 240 may execute based on determining that conditions of the program have been met. In some implementations, interface 700 may present options for the user to select a condition, such as a particular mood, and device settings for one or more accessory devices 230 that may be applied when control device 240 identifies the particular mood (e.g., based on mood-related information received from sensory device 220). In the example shown in FIG. 7A, user device 210 may receive a selection of a mood (e.g., a "Mellow" mood), and settings for three accessory devices 230 (e.g., accessory device 230-1, accessory device 230-2, and accessory device 230-3). In FIGS. 7A-7C, assume that accessory device 230-1 is a music player, accessory device 230-2 a scented oil diffuser, and that accessory device 230-3 is a light controller.

As shown in FIG. 7A, user device 210 may receive program instructions corresponding to device 1 settings, device 2 settings, and device 3 settings (corresponding to device settings for accessory device 230-1, accessory device 230-2, and accessory device 230-3, respectively). For example, user device 210 may receive device 1 settings to direct accessory device 230-1 to play a particular song (e.g., the song file "Song 1.mp3"), device 2 settings to direct accessory device 230-2 to diffuse a particular scent (e.g., a lavender scent), and device 3 settings to direct accessory device 230-3 to set a brightness level of a light (e.g., to a brightness level of 35%).

In some implementations, user device 210 may provide the program instructions to control device 240. In some implementations, control device 240 may generate a program based on the program instructions. Alternatively, user device 210 may generate the program, based on receiving the program instructions via interface 700, and provide the program to control device 240.

Referring to FIG. 7B, control device 240 may identify that a condition has been met (e.g., a condition that a "Mellow" mood has been identified based on mood-related information provided by sensory device 220). Based on identifying that the condition has been met, control device 240 may execute the program to apply device settings to accessory device 230-1, accessory device 230-2, and accessory device 230-3 in accordance with the program. For example, control device 240 may apply settings to accessory device 230-1 to cause accessory device 230-1 to play a particular audio file (e.g., the audio file "Song 1.mp3"). Further, control device 240 may apply settings to accessory device 230-2 to cause accessory device 230-2 to diffuse a particular scent (e.g., a lavender scent). Also, control device 240 may apply setting to accessory device 230-3 to cause accessory device 230-3 to set a brightness level of a light to 35%.

In some implementations, control device 240 may receive an indication of a selection, from user device 210, identifying a user's mood. For example, referring to FIG. 7C, user device 210 may receive the selection from a user via interface 700. Based on receiving the selection, user device 210 may provide an indication of the selection to control device 240 and control device 240 may execute a corresponding program, associated with the selection of the user's mood to apply settings to accessory device 230-1, accessory device 230-2, and accessory device 230-3.

While a particular example is shown in FIGS. 7A-7C, the above description is merely an example implementation. In practice, other examples are possible from what is described above in FIGS. 7A-7C. Also, while a particular format of interface 700 is shown, in practice, interface 700 may have a different format and appearance than what is shown.

As described above, control device 240 may generate a program by correlating device settings with conditions under which the device settings are applied. Additionally, or alternatively, a user may provide a program to control device 240 (e.g., a program that directs control device 240 to apply device settings to particular accessory devices 230 based on particular conditions, such as conditions relating to the user's schedule and/or mood). In some implementations, control device 240 may update a program (either a generated program or a user provided program) to adapt to the user's habits by monitoring the device settings of accessory devices 230 and the conditions under which the device settings are applied. In some implementations, a program may identify a sequence in which to apply the device settings. As a result, settings of accessory devices 230 may be automatically applied (e.g., based on the user's habits/behaviors) to power on/off accessory devices 230 and/or cause accessory devices 230 to perform particular functions in a particular order based on a user's schedule, a user's mood, a time of day, weather information, geographic location, and/or some other condition.

The foregoing description provides illustration and description, but is not intended to be exhaustive or to limit the possible implementations to the precise form disclosed. Modifications and variations are possible in light of the above disclosure or may be acquired from practice of the implementations.

It will be apparent that different examples of the description provided above may be implemented in many different forms of software, firmware, and hardware in the implementations illustrated in the figures. The actual software code or specialized control hardware used to implement these examples is not limiting of the implementations. Thus, the operation and behavior of these examples were described without reference to the specific software code—it being understood that software and control hardware can be designed to implement these examples based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

Some implementations are described herein in conjunction with thresholds. The term "greater than" (or similar terms), as used herein to describe a relationship of a value to a threshold, may be used interchangeably with the term "greater than or equal to" (or similar terms). Similarly, the term "less than" (or similar terms), as used herein to describe a relationship of a value to a threshold, may be used interchangeably with the term "less than or equal to" (or similar terms). As used herein, "satisfying" a threshold (or similar terms) may be used interchangeably with "being greater than a threshold," "being greater than or equal to a threshold," "being less than a threshold," "being less than or equal to a threshold," or other similar terms, depending on the context in which the threshold is used.

To the extent the aforementioned implementations collect, store, or employ personal information provided by individuals, it should be understood that such information shall be used in accordance with all applicable laws concerning protection of personal information. Additionally, the collection, storage, and use of such information may be subject to consent of the individual to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

No element, act, or instruction used in the present application should be construed as critical or essential unless explicitly described as such. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise.

What is claimed is:

1. A method comprising:
receiving, by a first device, information identifying settings that are applied by a user to one or more second devices over a period of time,
the one or more second devices being non-mobile devices associated with one or more particular facilities;
receiving, by the first device and from one or more third devices, information regarding one or more user-related conditions and one or more environmental conditions,
the one or more third devices including a plurality of sensory devices,
the one or more user-related conditions being based on physiological measurements relating to a mood or a physical state of the user, and
the one or more environmental conditions being based on an environment associated with the one or more second devices;
determining, by the first device and based on the information regarding the one or more user-related conditions and the one or more environmental conditions, a pattern of one or more conditions under which the settings are applied by the user to the one or more second devices,
the one or more conditions including one or more of the one or more user-related conditions or the one or more environmental conditions;
storing, by the first device, information that correlates the settings, of the one or more second devices, with the one or more conditions;
receiving, by the first device, additional information from a sensory device, of the plurality of sensory devices, after storing the information that correlates the settings with the one or more conditions;
determining, by the first device, that at least one of the one or more conditions is met based on the additional information from the sensory device; and
applying, by the first device and without interaction of the user, at least one of the settings to at least one of the one or more second devices based on determining that the at least one of the one or more conditions is met.

2. The method of claim 1, where applying the settings causes the one or more second devices to power on or power off in a particular sequence.

3. The method of claim 1, where applying the settings causes the one or more second devices to output a particular amount of power or perform a particular function.

4. The method of claim 1, where the one or more environmental conditions include one or more conditions relating to weather information, a day, or a time of day.

5. The method of claim 1, where the one or more second devices include a home appliance or consumer electronics device connected to a same network as the first device.

6. The method of claim 1, further comprising:
receiving an update to the settings of the one or more second devices based on applying the settings;
storing information that correlates the update to the settings to the one or more conditions,
the update to the settings corresponding to updated settings; and
applying the updated settings to the one or more second devices when the at least one of the one or more conditions is met.

7. The method of claim 1, further comprising:
generating a condition score based on determining that the at least one of the one or more conditions is met; and
determining that the condition score satisfies a threshold,
wherein applying the settings to the one or more second devices is based on determining that the condition score satisfies the threshold.

8. A system comprising:
a first device to:
receive information identifying settings that are applied by a user to one or more second devices over a period of time,
the one or more second devices being non-mobile devices associated with one or more particular facilities;
receive, from a plurality of sensory devices, information regarding one or more user-related conditions and one or more environmental conditions,
the one or more user-related conditions being based on physiological measurements relating to a mood or a physical state of the user, and
the one or more environmental conditions being associated with an environment associated with the one or more second devices;
determine, based on the information regarding the one or more user-related conditions and the one or more environmental conditions, a pattern of one or more conditions under which the settings are applied by the user to the one or more second devices,
the one or more conditions including one or more of the one or more user-related conditions or the one or more environmental conditions;
store information that correlates the settings, of the one or more second devices, with the one or more conditions;
receive, from a sensory device of the plurality of sensory devices, additional information after storing the information that correlates the settings with the one or more conditions;
determine that at least one of the one or more conditions is met based on the additional information from the sensory device; and
apply, without interaction of the user, at least one of the settings to at least one of the one or more second devices based on determining that the at least one of the one or more conditions is met.

9. The system of claim 8, where, when applying the at least one of the settings, the first device is to apply the settings to cause the one or more second devices to power on or power off in a particular sequence.

10. The system of claim 8, where, when applying the at least one of the settings, the first device is to apply the settings to cause the one or more second devices to output a particular amount of power or perform a particular function.

11. The system of claim 8, where the one or more second devices include a home appliance or consumer electronics device connected to a same network as the first device.

12. The system of claim 8, where the first device is further to:
generate a condition score based on determining the at least one of the one or more conditions is met; and
determine that the condition score satisfies a threshold,
wherein, when applying the at least one of the settings to the one or more second devices, the first device is to apply the settings based on determining that the condition score satisfies the threshold.

13. The system of claim 8, where the physiological measurements further include voice-related information.

14. A non-transitory computer-readable medium for storing instructions, the instructions comprising:

a plurality of instructions which, when executed by one or more processors associated with a first device, cause the one or more processors to:
  receive information identifying settings that are applied by a user to one or more second devices over a period of time,
    the one or more second devices being non-mobile devices being associated with one or more particular facilities;
  receive, from a plurality of sensory devices, information regarding one or more user-related conditions and one or more environmental conditions,
    the one or more user-related conditions being based on physiological measurements relating to a mood or a physical state of the user, and
    the one or more environmental conditions being associated with an environment associated with the one or more second devices;
  determine, based on the information regarding the one or more user-related conditions and the one or more environmental conditions, a pattern of one or more conditions under which the settings are applied by the user to the one or more second devices,
    the one or more conditions including one or more of the one or more user-related conditions or the one or more environmental conditions;
  store information that correlates the settings, of the one or more second devices, with the one or more conditions;
  receive, from a sensory device of the plurality of sensory devices, additional information after storing the information that correlates the settings with the one or more conditions;
  determine that at least one of the one or more conditions is met based on the additional information from the sensory device;
  generate a condition score based on determining the at least one of the one or more conditions is met;
  determine that the condition score satisfies a threshold; and
  apply, without interaction of the user, at least one of the settings to at least one of the one or more second devices based on determining that the condition score satisfies the threshold.

15. The non-transitory computer-readable medium of claim 14, where one or more instructions, of the plurality of instructions, to apply the at least one of the settings cause the one or more processors to apply the settings to cause the one or more second devices to power on or power off in a particular sequence.

16. The non-transitory computer-readable medium of claim 14, where one or more instructions, of the plurality of instructions, to apply the at least one of the settings cause the one or more processors to apply the settings to cause the one or more second devices to output a particular amount of power or perform a particular function.

17. The non-transitory computer-readable medium of claim 14, where the one or more second devices include a home appliance or consumer electronics device connected to a same network as the first device.

18. The non-transitory computer-readable medium of claim 14, where the plurality of instructions further cause the one or more processors to:
  receive an update to the settings of the one or more second devices based on applying the settings;
  store information that correlates the update to the settings to the one or more conditions,
    the update to the settings corresponding to updated settings; and
  apply the updated settings to the one or more second devices when the at least one of the one or more conditions is met.

19. The non-transitory computer-readable medium of claim 14, where the plurality of sensory devices include one or more of:
  a biometrics monitoring device,
  a movement-tracker,
  a sleep-tracker, or
  a camera device.

20. The non-transitory computer-readable medium of claim 14, where the one or more environmental conditions include one or more of a lighting intensity, a room temperature, a noise level, or a sound level.

* * * * *